(12) United States Patent
Chung et al.

(10) Patent No.: US 8,974,805 B2
(45) Date of Patent: Mar. 10, 2015

(54) DENTAL CLEANSER COMPOSITION FOR IMPROVING ADHESION TO TEETH

(75) Inventors: Chong-Pyoung Chung, Seoul (KR);
Yoon-Jeong Park, Seoul (KR);
Jue-Yeon Lee, Gyeonggi-do (KR)

(73) Assignee: Nano Intelligent Biomedical Engineering Corporation, Seoul (KR)

( * ) Notice: Subject to any disclaimer, the term of this patent is extended or adjusted under 35 U.S.C. 154(b) by 320 days.

(21) Appl. No.: 13/581,073

(22) PCT Filed: Feb. 28, 2011

(86) PCT No.: PCT/KR2011/001384
§ 371 (c)(1),
(2), (4) Date: Oct. 31, 2012

(87) PCT Pub. No.: WO2011/105869
PCT Pub. Date: Sep. 1, 2011

(65) Prior Publication Data
US 2013/0224128 A1    Aug. 29, 2013

(30) Foreign Application Priority Data
Feb. 26, 2010 (KR) .................. 10-2010-0017500

(51) Int. Cl.
| | | |
|---|---|---|
| *A61Q 11/00* | (2006.01) | |
| *A61K 8/02* | (2006.01) | |
| *A61K 38/00* | (2006.01) | |
| *A61K 38/10* | (2006.01) | |
| *A61K 6/00* | (2006.01) | |
| *A61K 8/39* | (2006.01) | |
| *A61K 8/64* | (2006.01) | |
| *A61K 8/73* | (2006.01) | |
| *A61Q 17/00* | (2006.01) | |

(52) U.S. Cl.
CPC .............. *A61K 6/0035* (2013.01); *A61Q 11/00* (2013.01); *A61Q 17/005* (2013.01); *A61K 8/39* (2013.01); *A61K 8/64* (2013.01); *A61K 8/731* (2013.01)
USPC ................ 424/401; 424/49; 424/54; 514/1.1; 514/21.5

(58) Field of Classification Search
None
See application file for complete search history.

(56) References Cited

U.S. PATENT DOCUMENTS

| | | | |
|---|---|---|---|
| 5,217,950 A | 6/1993 | Blackburn et al. | |
| 5,260,271 A | 11/1993 | Blackburn et al. | |
| 5,304,540 A | 4/1994 | Blackburn et al. | |
| 5,334,582 A | 8/1994 | Blackburn et al. | |
| 5,629,282 A | 5/1997 | Bhakoo | |
| 5,691,301 A | 11/1997 | Blackburn et al. | |
| 5,753,614 A | 5/1998 | Blackburn et al. | |
| 2006/0204452 A1* | 9/2006 | Velamakanni et al. ......... 424/49 |
| 2007/0190176 A1* | 8/2007 | Percival et al. ............... 424/618 |
| 2008/0050398 A1* | 2/2008 | Bockmuehl et al. ....... 424/190.1 |

FOREIGN PATENT DOCUMENTS

| | | |
|---|---|---|
| EP | 0 722 327 B1 | 11/2000 |
| KR | 10-0143423 B1 | 7/1998 |
| KR | 10-0621191 B1 | 9/2006 |
| KR | 10-2007-0103761 A | 10/2007 |
| WO | WO 8912399 A1 * | 12/1989 |

OTHER PUBLICATIONS

Bekir Oğuz Aktener et al., "Smear Layer Removal with Different Concentrations of EDTA-Ethylenediamine Mixtures", Journal of Endodontics, May 1993, pp. 228-231, vol. 19, No. 5.
Lorenzo Breschi et al., "Immunocytochemical identification of Type I collagen in acid-etched dentin", J. Biomed Mater Res A., 2003, pp. 764-769, vol. 66, No. 4.
Kim A. Brogden, "Antimicrobial Peptides: Pore Formers or Metabolic Inhibitors in Bacteria?", Nature Reviews Microbiology, Mar. 2005, pp. 238-250, vol. 3.
Ole E. Sorensen et al., "Antimicrobial Peptides in Innate Immune Responses", Contrib Microbiol, 2008, pp. 61-77, vol. 15.
Yosef Rosenfeld et al., "Endotoxin (Lipopolysaccharide) Neutralization by Innate Immunity Host-Defense Peptides, Peptide Properties and Plausible Modes of Action", The Journal of Biological Chemistry, Jan. 20, 2006, pp. 1636-1643, vol. 281, No. 3.
Monisha G. Scott et al., "Interaction of Cationic Peptides with Lipoteichoic Acid and Gram-Positive Bacteria", Infect. Immun. 1999, pp. 6445-6453, vol. 67, No. 12.
Andrea Giacometti et al., "Potential Therapeutic Role of Cationic Peptides in Three Experimental Models of Septic Shock", Antimicrobial Agents and Chemotherapy, Jul. 2002, pp. 2132-2136, vol. 46, No. 7.
Beverly A. Dale et al., "Antimicrobial Peptides in the Oral Environment: Expression and Function in Health and Disease", Curr Issues Mol Biol., Jul. 2005, pp. 119-133, vol. 7, No. 2.

* cited by examiner

*Primary Examiner* — Tracy Vivlemore
*Assistant Examiner* — Monica Shin
(74) *Attorney, Agent, or Firm* — Rabin & Berdo, P.C.

(57) ABSTRACT

The present invention relates to a dental cleanser composition for improving adhesion to teeth, and more particularly to, a dental cleanser composition which functions to remove not only a smear layer from the dentin surface of an exposed tooth root, but also oral bacteria, and thus is effective in improving adhesion to teeth in periodontal surgery. The present invention provides a dental cleanser composition containing sodium ethylene diaminotetraacetate and octyl phenol ethoxylate which is a surfactant. Sodium ethylene diaminotetraacetate in the composition functions to remove a smear layer on the tooth root surface and has antibacterial activity, and octyl phenol ethoxylate in the composition functions to lipopolysaccharide. Thus, the composition improves adhesion to teeth in periodontal surgery.

4 Claims, 6 Drawing Sheets

SEQUENCE LISTING

```
<160> NUMBER OF SEQ ID NOS: 4

<210> SEQ ID NO 1
<211> LENGTH: 22
<212> TYPE: PRT
<213> ORGANISM: Artificial Sequence
<220> FEATURE:
<223> OTHER INFORMATION: human beta defensin 2 (BD2-2)

<400> SEQUENCE: 1

Cys Pro Arg Arg Tyr Lys Gln Ile Gly Thr Cys Gly Leu Pro Gly Thr
1               5                   10                  15

Lys Cys Cys Lys Lys Pro
            20

<210> SEQ ID NO 2
<211> LENGTH: 15
<212> TYPE: PRT
<213> ORGANISM: Artificial Sequence
<220> FEATURE:
<223> OTHER INFORMATION: human beta defensin 3(BD3-3)

<400> SEQUENCE: 2

Gly Lys Cys Ser Thr Arg Gly Arg Lys Cys Cys Arg Arg Lys Lys
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: human Platelet-derived growth factor subunit B
      (PDGF)

<400> SEQUENCE: 3

Arg Lys Ile Glu Ile Val Arg Lys Lys Pro Ile Phe Lys Lys Ala Thr
1               5                   10                  15

Val Thr

<210> SEQ ID NO 4
<211> LENGTH: 22
<212> TYPE: PRT
<213> ORGANISM: Artificial Sequence
<220> FEATURE:
<223> OTHER INFORMATION: human heparin-binding EGF-like growth factor
      (HB-EGF)
```

```
<400> SEQUENCE: 4

Cys Lys Arg Lys Lys Lys Gly Lys Gly Leu Gly Lys Lys Arg Asp Pro
1               5                   10                  15

Cys Leu Arg Lys Tyr Lys
            20
```

DENTAL CLEANSER COMPOSITION FOR IMPROVING ADHESION TO TEETH

TECHNICAL FIELD

The present invention relates to a dental cleanser composition for improving adhesion to teeth, and more particularly to, a dental cleanser composition which functions to remove not only a smear layer from the dentin surface of an exposed tooth root, but also oral bacteria, and thus is effective in improving adhesion to teeth in periodontal surgery.

BACKGROUND ART

Periodontal disease is a disease wherein soft tissue around teeth, and alveolar bone are destroyed by chronic inflammation caused by periodontal pathogens, so that the gum bleeds and teeth are loose and ultimately lost. Periodontal pathogens include *Prevotella intermedia, Actinomyces israelii, Fusobacterium nucleatum*, etc.

Efforts have been made to eliminate plaque-forming bacteria using antibiotics such as penicillin in order to prevent periodontal disease. However, these antibiotics are not used in clinical practice, because antibiotic-resistant bacteria are created when these antibiotics are used for a long period of time. To overcome this advantage, various methods comprising the use of fluorine-based compounds or automatic dental cleaning devices have been developed, but the effects thereof are insignificant.

A connective tissue attachment to normal periodontal tissue is composed of extracellular matrix complexes, such as the fibroblasts of gingival and periodontal ligaments, gingival epithelial cells, vascular endothelial cells, neurites, alveolar periodontal bone, collagen, glycoprotein, and proteoglycan. Periodontally diseased root surfaces can act as suitable matrices for loss of connective tissue attachment, loss of alveolar bone, contamination of the tooth root with bacteria and bacterial endotoxins, the change in the density and content of minerals, cell adhesion, and fibril development, thus causing pathological changes such as loss of chemotaxis to the required progenitor cells.

Thus, in order for regeneration of the tissue destroyed by periodontal disease, the environment of a root surface should be changed so that connective tissue cells can migrate and adhere to the root surface. Mechanical methods for treating the root surface include scaling and root planing.

However, a smear layer can be formed on the root surface after mechanical cleaning and can serve as a matrix, which can inhibit fibroblast attachment and connective tissue attachment and in which bacteria can grow, thus interfering with the healing of periodontal tissue. For this reason, methods have been conducted on methods of treating the tooth root using a tooth root cleaner. Dental cleansers (tooth root cleaners) are used to remove minerals from the root surface and to remove toxic substances induced by bacterial products.

Agents for cleaning the root surface, which have been studied, include citric acid, fibronectin, tetracycline hydrochloride (Tc-HCl), phosphoric acid, stannous fluoride, ethylene diamine tetraacetic acid (EDTA), chlorhexidine, formalin, cetylpyridinium chloride, sodium-N-lauroyl sarcosine, zinc iontophoresis, and the like.

Korean Patent Registration No. 621,191 (entitled "tooth cleaning composition containing polylysine") and Korean Patent Laid-Open publication No. 2007-0103761 (entitled "anti-corrosive cleaner composition and use thereof for cleaning of dental and medical devices") disclose that the use of acidic chemical agents, such as citric acid, tetracycline-HCl, in many animal tests, has positive effects on the regeneration of periodontal tissue, including effects on the removal of a smear layer, the opening of dentinal tubules, the exposure of a collagen matrix by decalcification of intertubular dentin, the removal of endotoxin, and antibacterial activity.

However, a series of clinical studies reported that these chemical substances did not show a significant improvement, and could result in tooth root resorption, bony ankylosis, tissue necrosis and gingival recession during a healing process, and could interfere with the restoration of alveolar bone. Thus, there has been a need to develop other methods for treating the root surface, which can promote the healing of connective tissue.

Accordingly, the present inventors have made extensive efforts to solve the above-described problems occurring in the prior art and, as a result, have found that a composition comprising the nonionic surfactant octyl phenol ethoxylate and sodium ethylene diaminotetraacetate functions removes not only a smear layer from the tooth root, but also oral bacteria and lipopolysacchride, and thus improves adhesion to teeth in periodontal surgery, thereby completing the present invention.

DISCLOSURE OF INVENTION

It is a main object of the present invention to provide a dental cleanser composition, which functions to demineralize a smear layer on the dentin surface of the tooth root, has antibacterial activity against periodontal pathogens, and functions to remove lipopolysaccharide, thus improving adhesion to teeth.

To achieve the above object, the present invention provides a dental cleanser composition which contains, as active ingredients, sodium ethylene diaminotetraacetate and octyl phenol ethoxylate which is a nonionic surfactant.

BRIEF DESCRIPTION OF THE DRAWINGS

FIG. 1 is a set of scanning electron microscope photographs of the surfaces of dentin blocks, wherein FIG. 1a is a photograph of a dentin block not treated with anything, FIG. 1b is a photograph of a dentin block treated with a dental cleanser composition, and FIG. 1c is a photograph of a dentin block treated with PrefGel.

FIG. 3 is a set of scanning electron microscope photographs showing cells attached to dentin blocks, wherein FIG. 3a is a photograph showing cells attached to a dentin block not treated with anything, FIG. 3b is a photograph showing cells attached to a dentin block treated with a dental cleanser composition, and FIG. 3c is a photograph showing cells attached to a dentin block treated with PrefGel.

FIG. 4 is a set of photographs showing the degree of distribution of exposed type I collagen, wherein FIG. 4a shows the degree of distribution of type I collagen in a dentin block not treated with anything, FIG. 4b shows the degree of distribution of type I collagen in a dentin block treated with a dental cleanser composition, and FIG. 4c shows the degree of distribution of type I collagen in a dentin block treated with PrefGel.

BEST MODE FOR CARRYING OUT THE INVENTION

Figure 1:
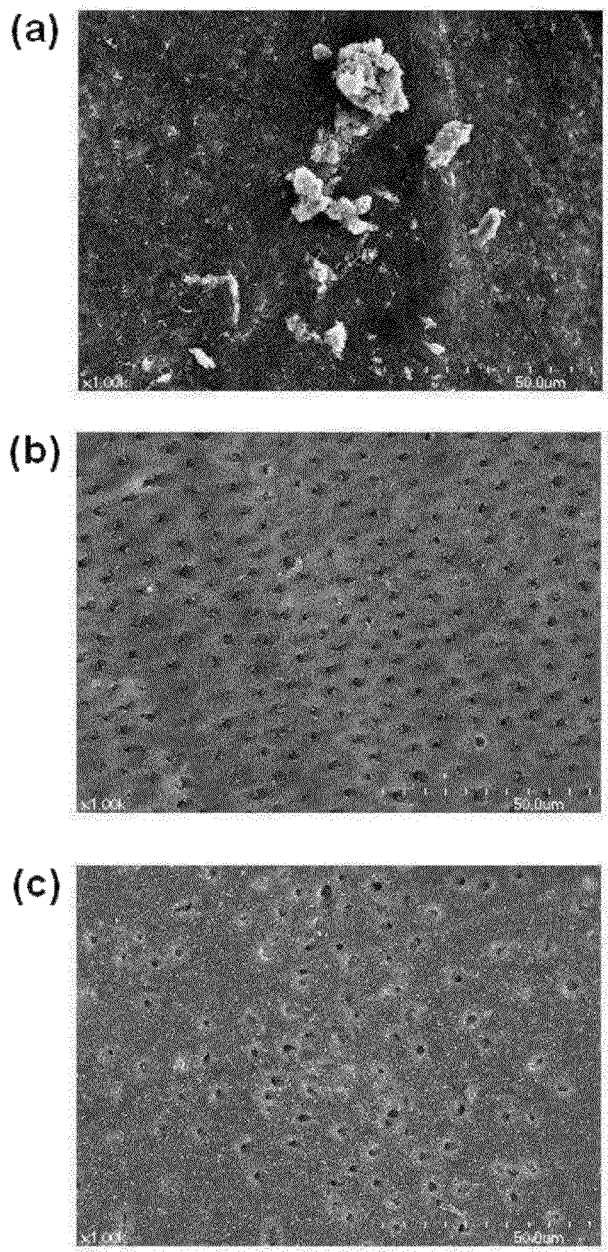

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The present invention is directed to a dental cleanser composition which contains, as active ingredients, sodium ethylene diaminotetraacetate and octyl phenol ethoxylate.

A dental cleanser composition according to the present invention functions to remove a smear layer on an exposed dentin surface by demineralization, has antibacterial activity against periodontal pathogens, and can be used to remove lipopolysaccharide.

Sodium ethylene diaminotetraacetate is a compound that forms chelates with divalent cations, such as $Ca^{2+}$, $Mg^{2+}$, $Fe^{2+}$, and $Pb^{2+}$ at a neutral pH. It was reported that sodium ethylene diaminotetraacetate can react with calcium ions in dentin to form a calcium complex which removes a smear layer formed upon root planing, and it can expose a fresh collagen matrix, which can promote the migration of fibroblasts by chemotaxis and can provide a place which maintaining a biologically active growth factor (Aktener B O, et al., Smear layer removal with different concentrations of EDTA-ethylenediamine mixtures. *J Endod*, 1993; 19(5):228-31, Breschi L. et al., Immunocytochemical identification of type I collagen in acid-etched dentin. *J Biomed Mater Res A*, 2003; 66(4):764-9.).

Sodium ethylene diaminotetraacetate which is used in the present invention has the effect of removing minerals from the root surface, as well as an antibacterial effect.

In the present invention, octyl phenol ethoxylate $(C_{14}H_{22}O(C_2H_4O)_n)$ a nonionic surfactant, has a hydrophilic polyethylene oxide group and a hydrophobic 4-(1,1,3,3-tetramethylbutyl)-phenyl group and is frequently used as a detergent in the biochemical field. At a concentration of 0.1-5%, octyl phenol ethoxylate permeabilizes the cell membrane in immunostaining, and at a concentration of 1%, it permeabilizes the cell wall of bacteria.

Octyl phenol ethoxylate which is used in the present invention has the effect of removing lipopolysaccharide (LPS). Other nonionic surfactants which are frequently used in the art include polyoxyethylene, Tween, Span, and the like, but the results of measurement of their effects on the removal of lipopolysaccharide indicated that octyl phenol ethoxylate has the best effect on the removal of lipopolysaccharide.

The dental cleanser composition according to the present invention contains, based on 100 parts by weight of the composition, 18-30 parts by weight of sodium ethylene diaminotetraacetate and 1-2 parts by weight of octyl phenol ethoxylate. If the content of sodium ethylene diaminotetraacetate in the composition is less than 18 parts by weight, the effect of removing minerals will be insignificant, and if it is more than 30 parts by weight, the effect of removing minerals will no longer increase. In addition, if the content of octyl phenol ethoxylate in the composition is less than 1 part by weight, it will have no effect on the removal of lipopolysaccharide (LPS), and if it is more than 2 parts by weight, the effect of removing lipopolysaccharide will no longer increase.

The dental cleanser composition according to the present invention may further contain an antibacterial peptide.

Antibacterial peptides are present in the human innate immune system, bind to the cell membrane and perforate the cell membrane, thereby exhibiting a wide range of antibacterial activities against bacteria, fungi and viruses (Brogden K A. Antimicrobial peptides: pore formers or metabolic inhibitors in bacteria, *Nat Rev Microbiol*, 2005; 3:238.50., Sorensen O E. et al., Antimicrobial peptides in innate immune responses, *Contrib Microbiol* 2008; 15:61.77.). Any antibacterial peptide also functions to neutralize the activity of LPS (Rosenfeld Y, Papo N, Shai Y. Endotoxin(lipopolysaccharide) neutralization by innate immunity host-defense peptides, Peptide properties and plausible modes of action, *J Biol Chem* 2006; 281:163643).

Antibacterial peptides are produced in a variety of cells, including epithelial cells, neutrophils, and salivary gland, which are involved in infection. Among them, cationic and hydrophobic antibacterial peptides include human defensin, cathelicidin LL-37, and histatin. Cationic peptides are known to prevent septicemia and inflammation caused by gram-negative and gram-positive bacteria (Scott M G. et al., Interaction of cationic peptides with lipoteichoic acid and Gram-positive bacteria., *Infect Immun*, 1999; 67:6445.53., Giacometti A. et al., Potential therapeutic role of cationic peptides in three experimental models of septic shock., *Antimicrob Agents Chemother*, 2002; 46:2132.6.).

An antibacterial peptide that may be used in the dental cleanser composition according to the present invention is selected from the group consisting of human α-defensin, human β-defensin, cathelicidin LL-37, and histatin, which have the amino acid sequences of SEQ ID NOs: 1 to 4 below:

```
SEQ ID NO: 1 (BD2-2):
C-P-R-R-Y-K-Q-I-G-T-C-G-L-P-G-T-K-C-C-K-K-P

SEQ ID NO: 2 (BD3-3):
G-K-C-S-T-R-G-R-K-C-C-R-R-K-K

SEQ ID NO: 3 (PDGF):
R-K-I-E-I-V-R-K-K-P-I-F-K-K-A-T-V-T

SEQ ID NO: 4 (HB-EGF):
C-K-R-K-K-G-K-G-L-G-K-K-R-D-P-C-L-R-K-Y-K
```

In the present invention, the antibacterial peptide may be contained in an amount of $3\times10^{-5}$ to $10^{-3}$ parts by weight based on 100 parts by weight of the dental cleanser composition. If the content of the antibacterial peptide in the composition is less than $3\times10^{-5}$ parts by weight, the antibacterial effect of the composition will be insignificant, and if it is more than $10^{-3}$ parts by weight, the antibacterial effect of the composition will no longer increase.

The dental cleanser composition according to the present invention may further contain one or more selected from the group consisting of propolis, xylitol, and protease. Herein, propolis or xylitol can improve the sensory properties of the composition, and protease can enhance the antibacterial effect of the composition and the effect on the removal of lipopolysaccharide.

The dental cleanser composition according to the present invention may contain pharmaceutically acceptable excipients (e.g., starch, lactose, calcium carbonate, calcium phosphate, etc.), binders (e.g., starch, gum Arabia, carboxymethylcellulose, hydroxymethylcellulose, crystalline cellulose, etc.), lubricants (e.g., magnesium stearate, talc, etc.), disintegrants (e.g., calcium carboxymethylcellulose, talc, synthetic aluminum silicate, etc.), diluents (e.g., water, vegetable oil, etc.), or a mixture of two or more thereof. Preferably, sodium carboxymethyl cellulose may be used in the composition of the present invention.

The formulation of the dental cleanser composition of the present invention is not specifically limited, but the composition of the present invention may be formulated into powders, fine granules, liquids, sprays, ointments or gels. Among these formulations, the gel formulation is preferred.

The dental cleanser composition of the present invention functions to demineralize a smear layer on an exposed dentin surface, has antibacterial activity against periodontal pathogens and is used to remove lipopolysaccharide (LPS), which is present on the cell wall of gram-positive bacteria and causes inflammation. More specifically, sodium ethylene diaminotetraacetate functions to remove a smear layer in the root surface and has antibacterial activity against periodontal pathogens, and the surfactant octyl phenol ethoxylate functions to remove lipopolysaccharide.

Periodontitis is a chronic disease wherein periodontal tissue is destroyed by periodontal pathogens. For regeneration of new periodontal tissue, new connective tissue should be attached to the root surface, and this process is achieved by the migration of fibroblasts and the attachment of collagen fibrils to the root surface. When the dental cleanser composition of the present invention is used, it demineralizes the root surface, and the demineralized root surface can serve as a place for storing physiologically active extracellular matrix proteins and growth factors and can a positive environment for wound healing. In addition, the exposed matrix proteins can induce mineralization to cause the regeneration of cementum and bone, thus improving adhesion to teeth.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Dental Cleanser Composition 3 g of sodium carboxymethyl cellulose was dissolved in 70 ml of distilled water to prepare a CMC solution. 24 g of EDTA-2Na and 1 mL of octyl phenol ethoxylate (Triton X-100) (Sigma, USA) were added to and mixed with the CMC solution, and the mixture was autoclaved, thereby preparing a dental cleanser composition.

Example 2

Preparation of Dental Cleanser Composition Containing Antibacterial Peptide

1 μg of an antibacterial peptide shown by SEQ ID NO: 2 was mixed with 1 ml of the dental cleanser composition prepared in Example 1, thus preparing a dental cleanser composition containing the antibacterial peptide.

SEQ ID NO: 2 (BD3-3):
G-K-C-S-T-R-G-R-K-C-C-R-R-K-K

Test Example 1

Scanning Electron Microscopic Observation of Tooth Surface to which Dental Cleanser was Applied A tooth was obtained from a patient in the Department of Periodontology, the Seoul National University Dental Hospital, according to the guideline of the Dental Hospital. Using a low-speed diamond saw, the crown portion was removed and the tooth was vertically cut into three specimens (4 mm×4 mm×1 mm in size). The dentin blocks were polished, and then stored in PBS (pH 7.4) at 4° C. until use. One of the dentil blocks was treated with the dental cleanser composition (prepared in Example 1) for 2 minutes and washed three times with distilled water. In addition, a negative control was a dentin block not treated with the dental cleanser composition, and a positive control was a dentin block treated with PrefGel (Biora, Sweden).

The dentin blocks were fixed with 2% glutaraldehyde in PBS for 15 minutes and post-fixed with 1% $OsO_4$ in 0.1 M PBS buffer at room temperature for 30 minutes. The dentin blocks were dehydrated with ethanol, after which these were freeze-dried and coated with gold. The surfaces of the dentin blocks were observed with a field emission scanning electron microscope (FE-SEM, Jeol, S-4700, Japan).

FIG. 1 is a set of scanning electron microscope photographs showing the surfaces of the dentin blocks treated with each of the samples. As can be seen in FIG. 1, in the dentin block not treated with anything, the smear layer on the surface remained unchanged (see FIG. 1a), and in the dentin block treated with the dental cleanser composition (Clinplant), the smear layer on the surface was removed (see FIG. 1b). In addition, in the dentin block treated with PrefGel, the smear layer was removed, but the degree of the removal of the smear layer was not greater than that for the dental cleanser composition of the present invention (see FIG. 1c).

Test Example 2

Test for Antibacterial Activity of Dental Cleanser Composition

Each of *Prevotella intermedia, Actinomyces israeili* and *Fusobacterium nucleatum* was cultured in a tryptic soy broth. The bacterial cells were diluted with PBS, and $10^5$ to $10^7$ bacterial cells/ml were spread onto tryptic soy agar plates and cultured at 37° C. for 24 hours.

Each of PBS, hexamedine (0.5% chlorhexidine), the dental cleanser composition (Clinplant) prepared in Example 1, the antibacterial peptide-containing dental cleanser composition prepared in Example 2, and PrefGel (Biora, Sweden) was added to a 6-mm filter paper disk (Whatman) and placed directly on the plates on which the bacterial cells had been cultured. The bacterial cells were incubated in an anaerobic incubator for 5 days, and then the inhibition of the diameter of the bacterial growth inhibition was measured.

Figure 2:
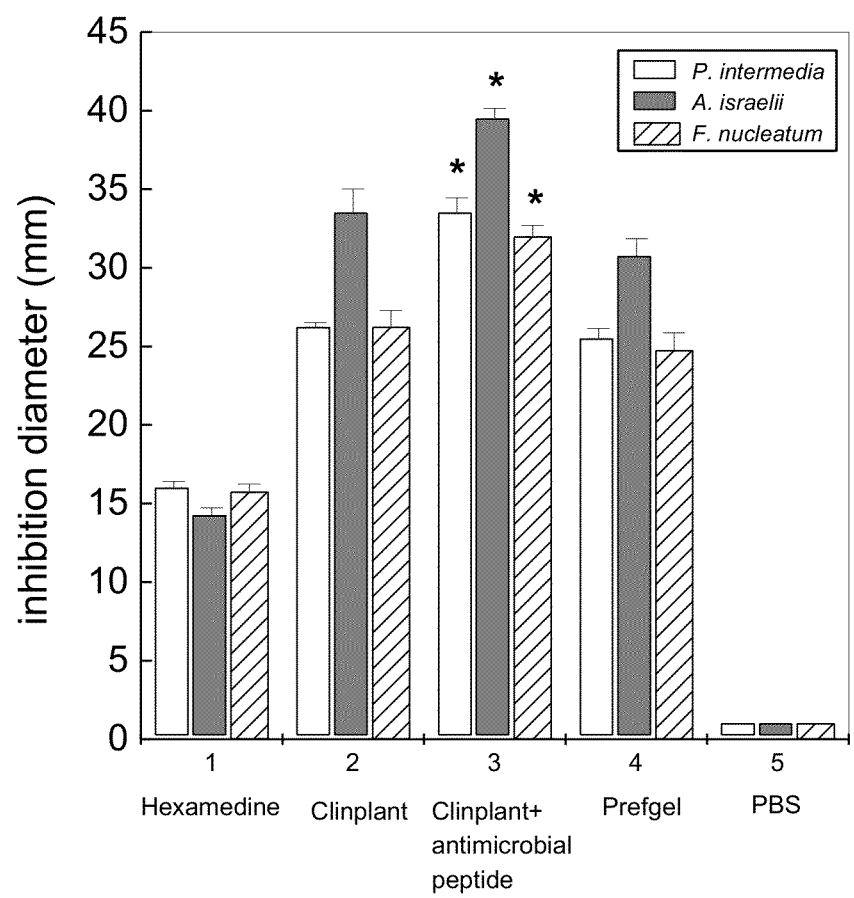
FIG. 2 is a graphic diagram showing the results of measuring the diameter of the bacterial growth inhibition caused by each sample.

FIG. 2 shows the results of the diameter of the bacterial growth inhibition caused by each of the samples. As can be seen therein, PBS did not inhibit the growth of the bacteria, and the dental cleanser composition (Clinplant) prepared in Example 1 had an inhibition diameter larger than the oral antibacterial agent hexamedine, suggesting that it had a higher antibacterial activity. In addition, the conventional product PrefGel and the dental cleanser composition (Clinplant) of Example 1 showed similar growth inhibition diameters, and the antibacterial peptide-containing Clinplant of Example 2 showed the highest antibacterial activity. This suggests that was added, the antibacterial effect of the dental cleanser composition containing the antibacterial peptide significantly increased compared to that of the dental cleanser composition containing no antibacterial peptide (*p<0.05, significant antibacterial activity compared to that of Clinplant).

Test Example 3

Cell Adhesion to Tooth Surface to which Dental Cleanser was Applied

NIH3T3 cells were cultured in α-MEM medium containing 10% FBS (Gibco) and 1% antibiotic-antimycotic solution (Gibco) in T75 flasks under the conditions of 37° C. and 5% $CO_2$.

A dentin block was treated with the dental cleanser composition (prepared in Example 1) for 2 minutes and washed three times with distilled water. A negative control was a dentin block not treated with the dental cleanser composition, and a positive control was a dentin block treated with PrefGel (Biora, Sweden). NIH3T3 cells were seeded onto each of the dentin blocks at a concentration of $5 \times 10^5$ cells/50 μl and cultured under the conditions of 37° C. and 5% $CO_2$ for 1 hours, and then 250 μl of medium was added thereto. After 1 day, each of the blocks was fixed with 2% glutaraldehyde in PBS for 15 minutes and post-fixed with 1% $OsO_4$ in 0.1 M PBS buffer at room temperature for 30 minutes. The dentin blocks were dehydrated with ethanol, after which these were freeze-dried and coated with gold. The surface of each of the dentin blocks was observed with a field emission scanning electron microscope (FE-SEM, Jeol, 5-4700, Japan).

Figure 3:
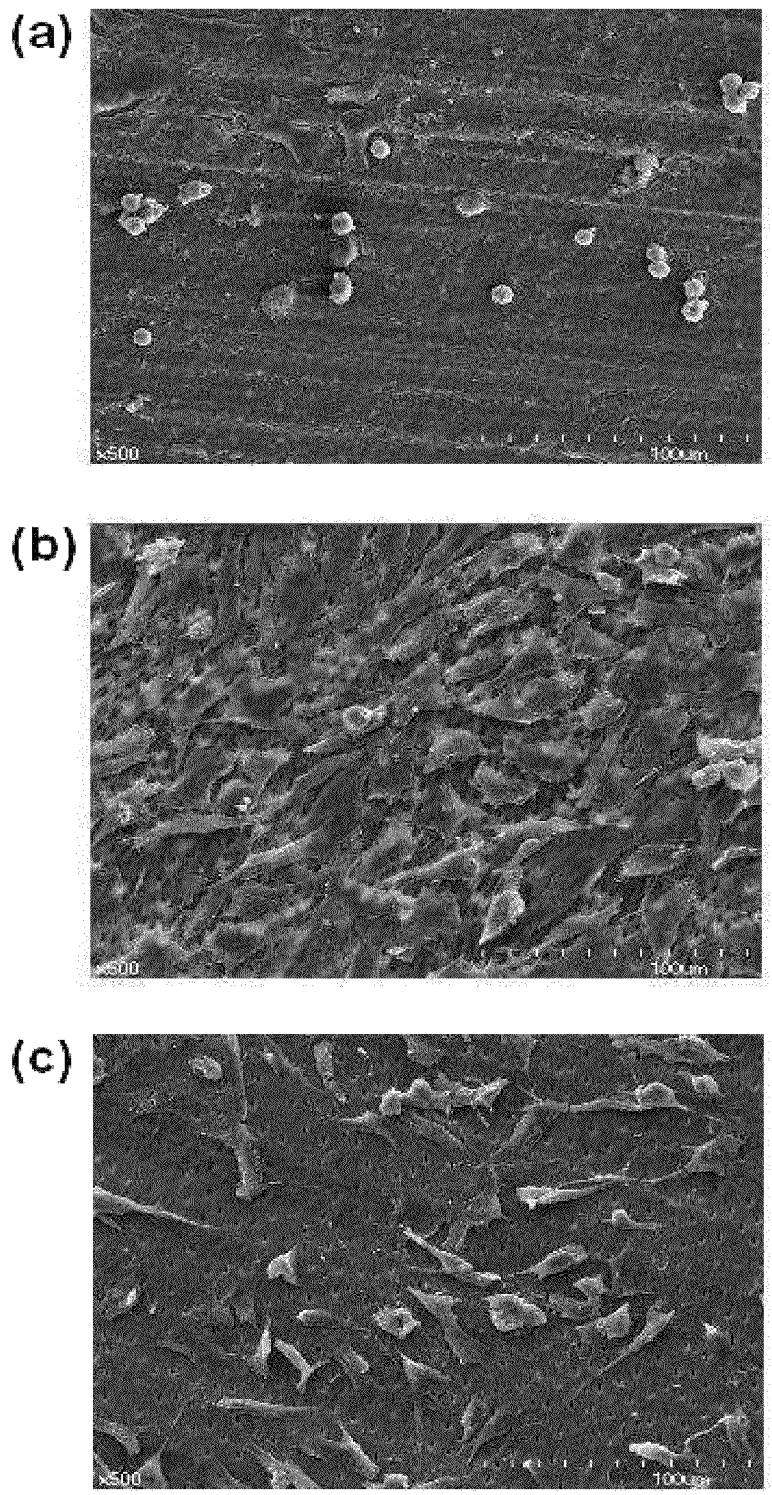

FIG. 3 is a set of scanning electron microscope photographs showing cells attached to each of the dentin blocks. As can be seen therein, in the dentin block not treated with anything, the number of cells attached thereto was not large, and the cells had a spherical shape, and thus were not firmly attached (see FIG. 3a). On the other hand, in the dentin block treated with the dental cleanser composition prepared in Example 1, a large number of cells were attached to the dentin block, and had a flattened shape, suggesting that the cells were stably attached (see FIG. 3b). In the dentin block treated with PrefGel, the degree of cell adhesion was similar to that for the dental cleanser composition (see FIG. 3c).

Test Example 4

Observation of Type I Collagen on Tooth surface to which dental cleanser composition was applied The dental cleanser composition prepared in Example 1 was applied to a dentin block for 2 minutes and washed, and then mouse monoclonal IgG anti-type I collagen (Sigma Chemical Co.) was used to measure collagen present on the root dentin block. The root dentin block was allowed to stand blocking buffer (1% BSA in PBS) at room temperature for 1 hour. Then, it was allowed to react with primary antibody (diluted at 1:500 in 1% BSA/PBS) at 4 r for 8 hours and washed three times with PBS for 10 minute each time. Then, it was allowed to react with secondary antibody (FITC conjugated goat anti-mouse IgG 1:1000 in 1% BSA/PBS) at room temperature for 1 hour and washed three times with PBS for 10 minute each time. The distribution of collagen on the dentin block was observed using a FLUOVIEW software (Olympus, Tokyo, Japan)-based Olympus FV-300 laser scanning microscope.

Figure 4:
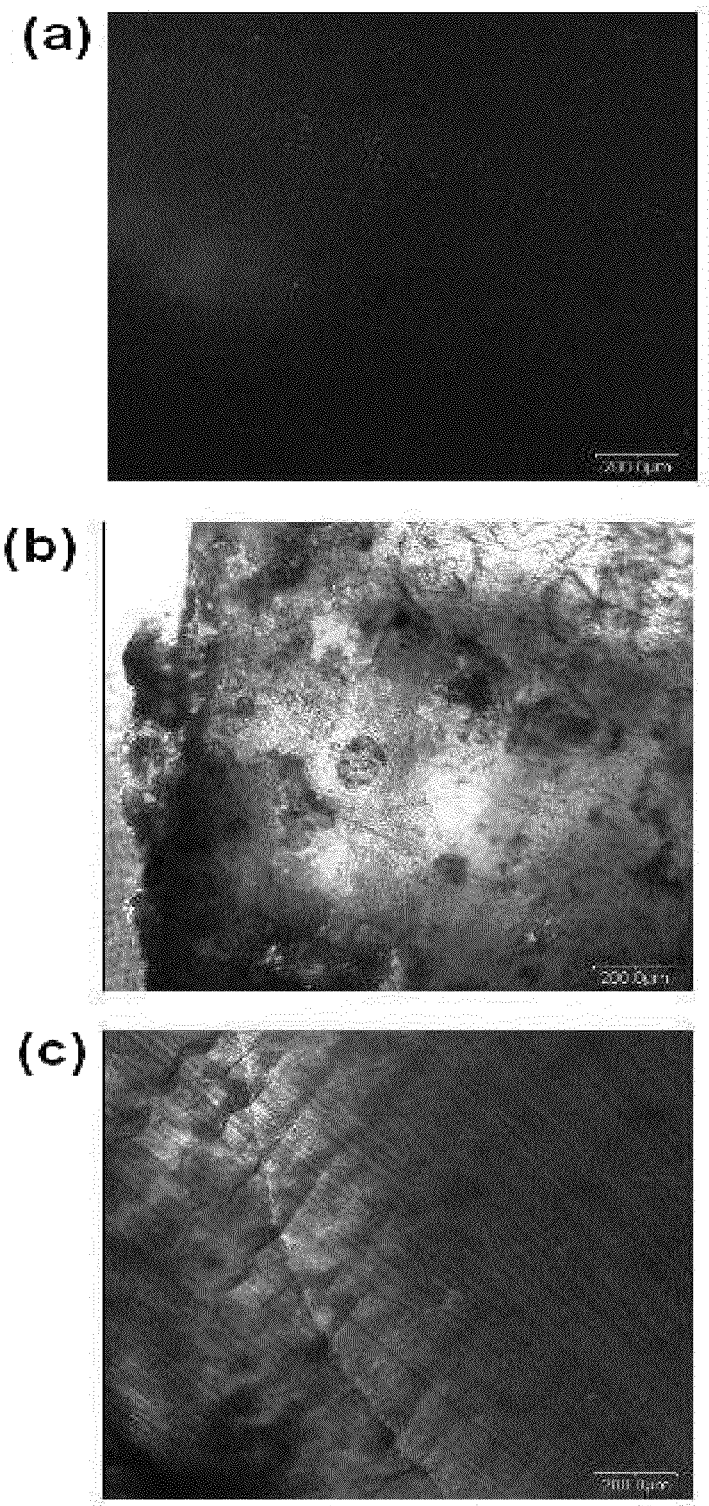

FIG. 4 is a set of photographs showing the degree of distribution of exposed type I collagen. As can be seen therein, in the dentin block not treated with anything, type I collagen could not be observed (see FIG. 4a), and in the dentin block treated with the dental cleanser composition prepared in Example 1, the fluorescence of FITC was widely distributed, suggesting that type I collagen was significantly exposed (see FIG. 4b). In the dentin block treated with PrefGel, the exposure of type I collagen was similar to that for the dental cleanser composition (see FIG. 4c).

Test Example 5

Measurement of Removal of Lipopolysaccharide by Dental Cleanser Composition

To measure the removal of bacterial lipopolysaccharide, a HEK-Blue LPS detection kit (InvivoGen, San Diego, Calif., USA) was used. 24-well plates were coated with 100 μg/ml of an LPS standard (*E. coli* K12 LPS) and allowed to stand at 4° C. for 8 hours. 200 μl of each of PBS, hexamedine (0.5% chlorohexidine), the dental cleanser composition (Clinplant) of Example 1, PrefGel (Biora, Sweden), the dental cleanser composition (CMC+EDTA) of Example 1, which contains no octyl phenol ethoxylate, and the dental cleanser composition (CMC+Triton-X100) of Example 1, which contains no EDTA-2Na, was applied to the plates for 2 minutes and washed three times with PBS. HEK-Blue cells were dispersed in detection media, after which the cells were seeded onto the plates at a density of $4 \times 10^4$ cells/well and cultured at 37° C. for 24 hours. The absorbance at a wavelength of 620 nm was measured using a microplate reader (BIO-TEK, Winooski, Vt., USA). The ratio of the remaining LPS was calculated using the absorbance of a lipopolysaccharide-free water-coated well as a blank.

Figure 5:
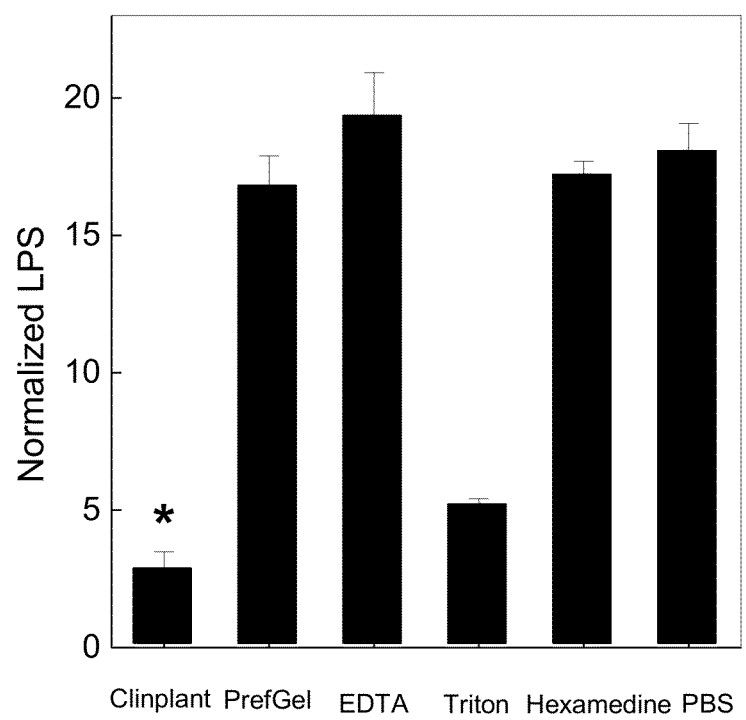
FIG. 5 is a graphic diagram showing the relative ratio of the remaining lipopolysaccharide (LPS) when a dental cleanser composition was used.

Relative absorbance ratio=absorbance of well treated with each sample/absorbance of well treated with endotoxin-free water FIG. 5 is a graphic diagram showing the relative ratios of to the remaining LPS standard. As can be seen in FIG. 5, the relative ratio of the LPS standard was the lowest in the presence of Triotn-X100, and EDTA had no effect on the removal of the LPS standard, and also Hexamedine and PrefGel had no effect on the removal of the LPS standard. However, in the case of the dental cleanser composition (Clinplant) of Example 1, which contains EDTA-2Na and Triton-X100, the ratio of the remaining LPS standard was lower than that in the case of treatment with Triotn-X100 alone, suggesting that EDTA-2Na and Triton-X100, which are contained in the dental cleanser composition of Example 1, exhibit a synergistic effect on the removal of the LPS standard.

Test Example 6

Measurement of Removal of Lipopolysaccharide by Nonionic Surfactant

To measure the removal of bacterial lipopolysaccharide, a HEK-Blue LPS detection kit (InvivoGen, San Diego, Calif., USA) was used. 24-well plates were coated with 100 μg/ml of an LPS standard (*E. coli* K12 LPS) and allowed to stand at 4° C. for 8 hours. Each of 1% Triton X-100 (Sigma), Span 80 (Sorbitan monooleate, M.W. 428, Sigma), Tween 20 (M.W. 1228, Sigma) and polyoxyethylene (M.W. 1400, Sigma) was applied to the plates for 2 minutes and washed three times with PBS. HEK-Blue cells were dispersed in detection media, after which the cells were seeded onto the plates at a density of $4 \times 10^4$ cells/well and cultured at 37° C. for 24 hours. The absorbance at a wavelength of 620 nm was measured using a microplate reader (BIO-TEK, Winooski, Vt., USA). The ratio of the remaining LPS standard was calculated using the absorbance of a lipopolysaccharide-free water-coated well as a blank.

Figure 6:
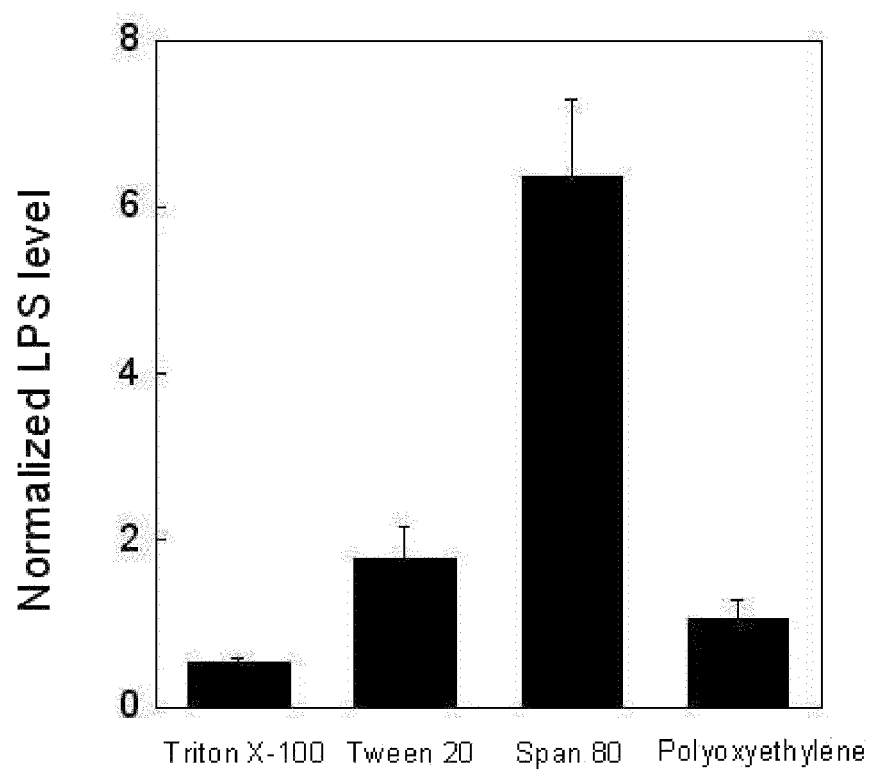
FIG. 6 is a graphic diagram showing the relative ratio of the remaining LPS when a non-ionic surfactant was used.

Relative absorbance ratio)=absorbance of well treated with each sample/absorbance of well treated with LPS-free water FIG. 6 is a graphic diagram showing the relative ratios of the remaining LPS standard. As can be seen in FIG. 6, the ratio of the remaining LPS standard was the lowest when the plates were treated with Triton X-100 (HLB 13), and the ratio of the remaining LPS standard was higher in the order of polyoxyethylene (HLB 10)<Tween 20 (HLB 16)<Span 80 (HLB 4). Thus, it can be seen that Triton X-100 was most effective in removing the LPS standard.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, the present invention provides a dental cleanser composition containing sodium ethylene diaminotetraacetate and octyl phenol ethoxylate which is a surfactant. Sodium ethylene diaminotetraacetate in the composition functions to remove a smear layer on the tooth root surface and has antibacterial activity, and octyl phenol ethoxylate in the composition functions to lipopolysaccharide. Thus, the composition improves adhesion to teeth in periodontal surgery.

What is claimed is:

1. A dental cleanser composition which contains, as active ingredients, sodium ethylene diaminetetraacetate; octyl phenol ethoxylate; sodium carboxymethyl cellulose; and an antibacterial peptide consisting of an amino acid sequence of SEQ ID NO: 2.

2. The dental cleanser composition of claim 1, wherein the sodium ethylene diaminetetraacetate and the octyl phenol ethoxylate are contained in an amount of 18-30 parts by weight and in an amount of 1-2 parts by weight, respectively, based on 100 parts by weight of the composition.

3. The dental cleanser composition of claim 1, wherein the antibacterial peptide is contained in an amount of $3 \times 10^{-5}$ to $10^{-3}$ parts by weight based on 100 parts by weight of the dental cleanser composition.

4. The dental cleanser composition of claim 1, which further contains one or more selected from the group consisting of propolis, xylitol, and protease.

* * * * *